United States Patent [19]

Holmes et al.

[11] Patent Number: 4,699,140

[45] Date of Patent: Oct. 13, 1987

[54] INSTRUMENT FOR INSERTING AN INTRAOCULAR LENS

[75] Inventors: Martin J. Holmes; Howard F. Newman, both of Los Angeles, Calif.

[73] Assignee: Iolab Corporation, Covina, Calif.

[21] Appl. No.: 753,732

[22] Filed: Jul. 10, 1985

[51] Int. Cl.[4] .............................................. A61B 17/00
[52] U.S. Cl. .................................... 128/303 R; 623/6
[58] Field of Search ............... 128/329 R, 321, 303 R, 128/330, 305, 130, 127; 623/4, 6; 604/21

[56] References Cited

U.S. PATENT DOCUMENTS

| | | | |
|---|---|---|---|
| 3,403,646 | 10/1968 | Goldman | 128/330 |
| 3,498,286 | 3/1970 | Polyamyi et al. | 604/21 |
| 3,518,993 | 7/1970 | Blake | 128/321 |
| 3,994,297 | 11/1976 | Kopf | 128/305 |
| 4,126,124 | 11/1978 | Miller | 128/330 |
| 4,139,011 | 2/1979 | Benoit et al. | 128/329 R |
| 4,144,876 | 3/1979 | DeLeo | 128/330 |
| 4,214,585 | 7/1980 | Bailey, Jr. | 128/303 R |
| 4,244,370 | 1/1981 | Furlow et al. | 128/303 R |
| 4,373,218 | 2/1983 | Schachar | 623/6 |
| 4,479,291 | 10/1984 | Yamada | 128/330 |

FOREIGN PATENT DOCUMENTS

0587932 1/1978 U.S.S.R. .............................. 128/305

Primary Examiner—Richard J. Apley
Assistant Examiner—H. Macey
Attorney, Agent, or Firm—Donal B. Tobin

[57] ABSTRACT

A surgical instrument to facilitate the insertion and allow better control of the superior haptic of an intraocular lens into the capsular bag of the eye. The instrument includes a hollow cannula with a beveled distal tip and a tapered slot extending proximally from the distal tip of the cannula. A stylet slides freely within the cannula and has a distal tip beveled at an angle corresponding to the bevel of the distal tip of the cannula. A handle is provided for supporting the cannula and the stylet and includes a mechanism for advancing the stylet distally to align the beveled distal tips of the cannula and the stylus to form a plane which resolves the forces exerted by the resilient haptic in a direction which urges the haptic into the capsular bag.

21 Claims, 11 Drawing Figures

INSTRUMENT FOR INSERTING AN INTRAOCULAR LENS

FIELD OF THE INVENTION

The present invention relates to an instrument for inserting an intraocular lens into the eye and more particularly to an instrument to facilitate the insertion of the haptic loops of an intraocular lens into the capsular bag of or into the anterior chamber of the eye.

BACKGROUND OF THE INVENTION

It is now commonly accepted that the vision impairing disease known as cataracts can be alleviated by surgically replacing the natural lens of the eye with an artificial intraocular lens. The condition of cataracts is characterized by a clouding or opacification of the natural lens of the eye so that the amount of light which reaches the retina is substantially reduced or completely eliminated.

Figure 1:
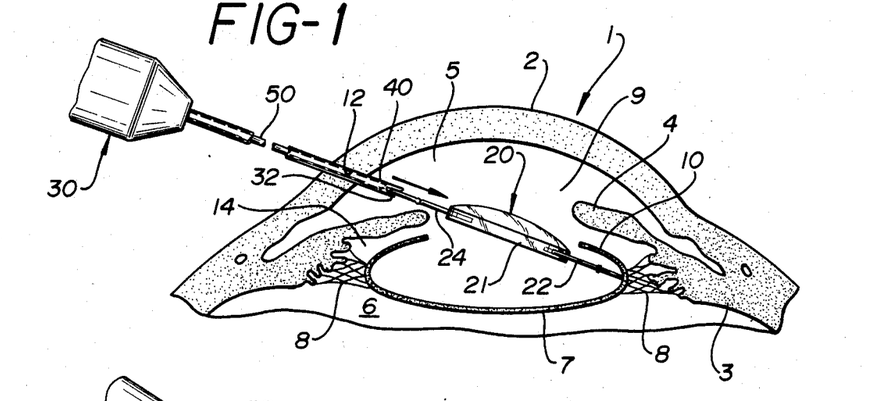
FIG. 1 shows a schematic cross-sectional view of the eye into which an intraocular lens is being inserted with the assistance of the instrument of the present invention.

The anatomy of the eye 1 is shown schematically in FIG. 1. The cornea 2 forms the front surface of the eye and connects with the ciliary muscle 3, from which the iris 4 extends. Iris 4 divides the front portion of the eye into the anterior chamber 5, between iris 4 and cornea 2, and a posterior chamber 6 behind the iris 4. The capsular bag 7 in which the natural lens of the eye is encased is supported from ciliary muscle 3 by suspensory ligaments 8, called zonules. Pupil 9 is the aperture at the center of iris 4 through which light passes to the posterior chamber 6 and to the back of the eye.

During cataract surgery, a portion of the anterior surface of capsular bag 7 is removed by well-known techniques leaving an anterior flap 10 at the anterior edges of capsular bag 7. The cataract lens (not shown) is then removed and the interior of the remaining capsular bag 7 is cleaned and polished by similarly well-known surgical techniques. The eye is now ready to receive an intraocular lens implant.

A variety of lenses are available for implantation into the eye. Some lenses have been designed for placement in anterior chamber 5. Other lenses have been specifically designed for placement in posterior chamber 6 and particularly in capsular bag 7 in posterior chamber 6. This patent application is directed to a medical instrument for facilitating the insertion of an intraocular lens into capsular bag 7 in the posterior chamber 6 of eye 1 behind iris 4. Thus, this application will focus on describing the use of the instrument for inserting a posterior chamber lens into the capsular bag. However, because of the ease of releasing the superior haptic of the lens with the instrument it is also believed to facilitate insertion into the anterior chamber of the eye.

Posterior chamber intraocular lenses 20 generally have two principal parts: a medial, light-focusing body 21 (also called the optic) made of a nontoxic, plastic material which will replace the natural lens of the eye and focus light on the retina; and, haptic support portions 22 and 24 which extend from optic 21 to the anatomy of the eye and provide a means for fixing and holding optic 21 in its proper position within the eye. Haptic support loops 22 and 24 are commonly made of a very flexible, resilient, filamentary plastic material like polypropylene.

In many instances, it is highly desirable to place the intraocular lens implant in capsular bag 7 in the same general position that the natural lens of the eye resided before removal.

As shown particularly in FIG. 1, the intraocular lens implant 20 is inserted through an incision 12 made in the base of cornea 2. The patient is usually lying on his back with the doctor standing facing the top of the patient's head. Incision 12 may be made at a position called the superior part of the eye. The intraocular lens is inserted from the superior portion of the eye toward the inferior portion of the eye. The first haptic to be inserted into the eye is called the inferior haptic. The second haptic to be inserted into the eye is called the superior haptic. This terminology of inferior position and superior position is generally used in the industry, and inferior positions are those spaced further away from the entrance incision, and superior positions are those spaced closer to the entrance incision.

The first haptic support 22, also called the inferior haptic, is inserted directly into the capsular bag 7. As the inferior haptic 22 is inserted into the eye, it can be easily slanted through pupil 9, and proper placement of the inferior loop in capsular bag 7 is relatively easy to achieve for the skilled surgeon. On the other hand, the other haptic support loop 24 (also known as the superior loop) can be difficult to insert in capsular bag 7.

A variety of existing tools are used to facilitate the insertion of the superior loop 24 in capsular bag 7. A tool with a small hook on the end can be used to push superior loop 24 in the direction of inferior loop 22. The natural resilience of the haptic loops 22 and 24 tend to hold superior loop 24 in the insertion hook. However, as the surgeon attempts to release superior loop 24 from the insertion hook, the natural resilience of superior loop 24 causes it to continue to engage the hook making it difficult for the surgeon to release superior loop 24 and still completely control its motion to assure placement of superior haptic 24 in capsular bag 7. Sometimes superior loop 24 will end up in the groove 14 between the posterior surface of iris 4 and ciliary muscle 3.

Many surgeons find that an angular rotation of the wrist or fingers is required to release the frictional engagement between superior haptic 24 and the tool, so that superior haptic 24 may slide off the tool into capsular bag 7. Such angular movement of the surgeon's wrist may cause either the intraocular lens 20 or the tool itself to touch portions of the interior anatomy of the eye. Touching the interior surface of cornea 2 is particularly undesirable because it is very delicate and easily damaged.

There are other difficulties associated with the use of such hooks. As the user grasps superior haptic 24 with the hook and urges it inferiorly, optic 21 tends to rotate and haptic 24 deflects laterally, both of which tend to cause haptic 24 to slide off such a hook. This makes it more difficult to maneuver superior haptic 24 to its desired portion. Similar difficulties are experienced when inserting an anterior chamber lens.

It would be desirable to have a surgical instrument which would facilitate the insertion of superior loop 24 into capsular bag 7 while minimizing the movement of the tool. It can be difficult to place superior haptic 24 in capsular bag 7, because capsular bag 7 is hard to reach and it cannot be easily visualized by the surgeon. Thus, even though superior haptic 24 may appear to be placed in the superior side of the capsular bag 7, it is very difficult to confirm that this is actually the case.

It would be desirable to have an insertion tool that would easily, quickly and reliability permit the surgeon to assure that he has placed superior haptic 24 of the lens 20 in capsular bag 7.

SUMMARY OF THE INVENTION

The present invention provides a surgical instrument with a specially designed tip to facilitate the insertion of the superior haptic loop of an intraocular lens into the capsular bag of the eye while minimizing the rotational movement of the surgeon's wrist or fingers and thereby minimizing the chance of touching the interior anatomy of the eye with the insertion tool or with the intraocular lens. This economy of wrist or finger movement also makes the instrument useful for inserting an anterior chamber lens.

The surgical instrument of the present invention has a specially designed tip which includes a hollow cannula with a proximal end and a distal end. The word "proximal" in this patent application will be used to indicate that portion of the element being described which is furthest from the eye and the word "distal" will be used to indicate that portion of an element which is closest to the eye. The distal tip of the annula is beveled at an angle to the adjacent wall of the cannula and includes a slot extending proximally from the distal tip for capturing one of the haptic loops of an intraocular lens while the loop is maneuvered into the posterior chamber. A stylet is placed for easy sliding within the lumen of the cannula and it also has a proximal end and a distal end. In the preferred embodiment, the distal tip of the stylet may also be beveled at an angle to the adjacent side wall of the stylet generally corresponding to the beveled angle of the distal end of the cannula. Although it is desirable to bevel the distal tip of the stylet, it is not considered necessary.

The distal end of the stylet resides in its rest position slightly proximally of the proximal end of the slot in the distal tip of the cannula. Means are provided for advancing the stylet distally until the distal tip, or preferably the beveled distal tip of the stylet is aligned with the distal tip of the cannula to eject the haptic loop from the cannula slot.

In those embodiments wherein the distal tips of both the cannula and the stylet are beveled at corresponding angles, means are provided to rotationally orient the distal tips of the cannula and the stylet so that the respective beveled tips of the cannula and the stylet are aligned to form a plane at the distal tip of the instrument.

In order to maneuver the superior loop 24 into capsular bag 7, a portion of superior haptic 24 is captured in the slot of the distal tip of the cannula. The instrument is then moved inferiorly into the eye so as to compress both of the haptics. When the stylet is advanced into alignment with the distal tip of the cannula, the forces stored in the resilient haptic loops impinge against the combined distal tips of the cannula and the stylet. The beveled distal tip of the cannula, and the combined beveled distal tips of the cannula and the stylet (in those embodiments where a beveled stylet is used) resolve the forces stored in the resilient superior haptic in a direction which urges the superior haptic 24 into capsular bag 7.

In the preferred embodiment, the cannula and the stylet are mounted in a handle. The cannula is rigidly attached to the handle, and the stylet is mounted to permit the stylet to reciprocate under the action of an advancing mechanism and a retraction mechanism, both associated with the handle.

In one embodiment, the handle has a generally cylindrical bore which bore has a proximal portion of one diameter and intermediate portion of a larger diameter and a distal portion of a still larger diameter. The proximal portion of the handle bore communicates with a transverse slot in the handle.

The proximal end of the stylet is fixed into a hub which has a proximal stem portion and an intermediate portion. The stem portion is slidably received in the proximal portion of the handle bore, and the intermediate portion of the stylet hub is slidably received in the intermediate portion of the handle bore.

The proximal portion of the cannula is fixed to a hub which is received in the distal portion of the handle bore and bottoms against a shoulder in the handle bore. A cap is fixed to the distal portion of the handle, preferably by cooperating threads on the handle and the cap to hold the cannula hub and cannula in place in the handle. A lever is pivotably mounted in the handle transverse slot and includes a cam surface which interacts with the proximal stem portion of the stylet hub to advance the stylet hub a predetermined distance against the biasing force of a spring disposed between the confronting proximal surface of the cannula hub and the distal surface of the stylet hub.

In another embodiment, the proximal stem of the hub may be omitted and the opening between the handle intermediate bore and the transverse slot enlarged so that the proximal end of the hub intermediate portion extends into the transverse slot to impinge directly on the cam surface of the lever.

It may be desirable in certain embodiments to include a curved portion on the cannula and to make the stylet of a flexible or prebent material so that it will readily conform to the curvature of the cannula.

It may also be desirable to provide the slot at the distal tip of the cannula with a taper so that the slot becomes narrower as one advances proximally along the slot. It is desirable that the maximum proximal width of the slot be less than the minimum diameter of the loop and that the minimum proximal width of the slot be greater than the maximum diameter of the loop. Such a tapered slot tends to hold superior haptic 24 in the tip of the instrument and reduces the tendency of haptic 24 to deflect laterally as it is compressed and optic 21 rotates. Further, the small included angle of the slot provides a wedging action on the haptic, preventing it from sliding sideways, and allowing better haptic control The means for maintaining the rotational orientation of the cannula with respect to the stylet are preferably keyways on each of the cannula and stylet hubs and corresponding key pins mounted on the handle. This anti-rotational feature would always be used for the cannula. This anti-rotational feature would only be used for the stylet if the distal tip of the stylet were beveled at an angle corresponding to that of the cannula.

Alternatively, the tip of the stylet could be prestressed so that it will bend when it clears the beveled tips of the cannula to urge the superior haptic of the lens more in the desired direction.

Alternatively, the stylet could be a fiber optic bundle suitably connected to a light source and a camera to illuminate and photograph the interior of the eye during lens insertion.

The manual lever actuation of the stylet could be mechanized by using, for example, a pneumatic actuator operated by a foot switch to advance the stylet.

The stylet could incorporate irrigation and/or aspiration channels through which fluid could be introduced to, or taken from the eye. The irrigation fluid could provide lubrication and additional thrust to urge the superior loop off the tip of the instrument.

These and other features and advantages of the present invention will become more apparent when taken in conjunction with the following detailed description of the preferred embodiments and the following drawings.

DETAILED DESCRIPTION OF THE PREFERRED EMBODIMENT

Referring now to FIG. 1, there is shown a schematic view of the anatomy of the eye with the instrument 30 of the present invention grasping superior haptic 24 of intraocular lens 20. Lens 20 is maneuvered into the position shown in FIG. 1 where inferior loop 22 is placed in the inferior portion of capsular bag 7, and superior loop 24 still remains outside the iris. The lens is maneuvered into this position by techniques well known to the skilled surgeon. Superior loop 24 is then captured in a slot 44 (see FIG. 4) in the distal tip 32 of instrument 30, while superior loop 24 is still outside the iris. Instrument 30 is advanced inferiorly moving the tip 32 along with superior haptic 24 into the eye. Tip 32 of instrument 30 is moved inferiorly until tip 32 passes the superior edge of the iris 4 and is past the superior edge of anterior flap 10 of capsule 7. As will be explained in greater detail later in the application, superior haptic 24 is ejected from slot 44 and slides into capsular bag 7.

The relative size of the parts of the eye and intraocular lens are not drawn to exact scale, nor is the relative position of tip 32 of insertion tool 30 shown in the precise position it would be used within the eye. These drawings are intended to demonstrate the use of the present invention but are not intended to be surgically correct.

Figure 3:
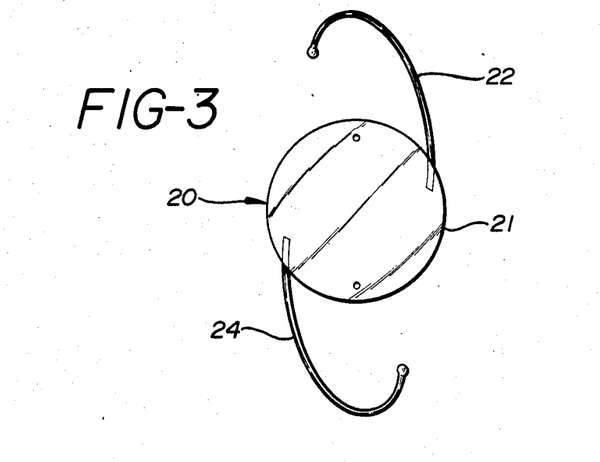
FIG. 3 shows an intraocular lens with which the instrument of the present invention may be used.

For informational purposes, there is shown in FIG. 3 a schematic representation of the kind of posterior chamber intraocular lens whose insertion into capsular bag 7 can be facilitated with the instrument 30 of the present invention. There are, of course, a variety of other posterior or anterior chamber lenses, many of which we believe would also be well adapted for insertion by instrument 30.

Figures 4, 5:
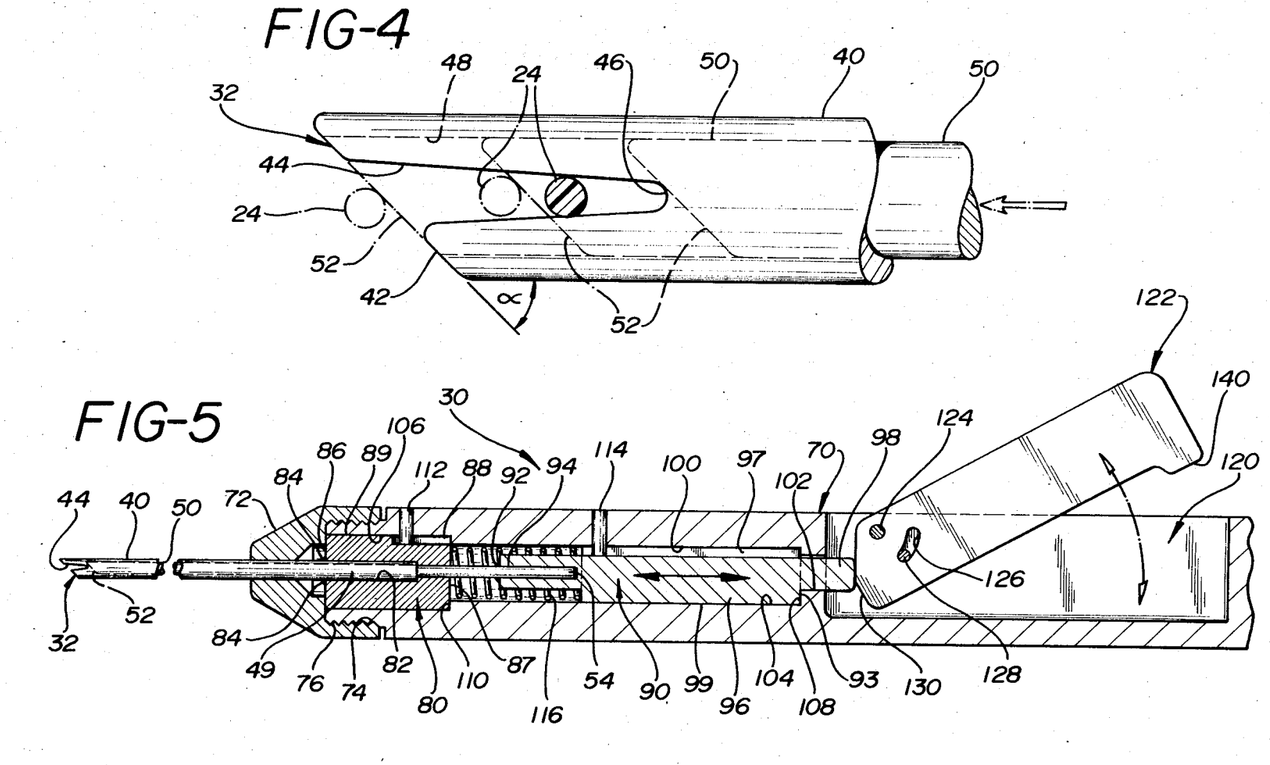
FIG. 4 shows a detailed view of the tip of the instrument of the present invention.
FIG. 5 shows a cross-sectional view of the instrument of the present invention.

Referring now to FIG. 4, there is shown a detailed view of the distal tip 32 of instrument 30. Instrument 30 includes a hollow cannula 40 having a beveled distal tip 42 disposed at an angle, preferably about 45°, although this angle is not critical, to the surrounding side wall of cannula 40. Letter "α" represents this angle and can be chosen at any convenient angle, preferably between about 30° to about 60°.

Distal tip 42 of cannula 40 includes a slot 44 extending from distal tip 42 in the proximal direction. Slot 44 is preferably tapered to become narrower as one advances proximally along the slot. The minimum width of slot 44 is preferably less than the diameter of haptic loop 24, and the maximum width of slot 44 is preferably greater than the diameter of haptic loop 24. The interior proximal end 46 of slot 44 includes a smoothly curved radius. All of the surfaces of the distal tip 42 and slot 44 of cannula 40 are smoothly polished to avoid damaging haptic loop 24 or any of the internal anatomy of the eye. In FIG. 4 there is shown in cross-section superior haptic loop 24, which is shown to have a generally circular cross-section, but this is not critical, and any convenient haptic loop configuration could be accommodated by various slot geometries. FIG. 4 illustrates that superior haptic 24 does not extend all the way to the proximal end 46 of slot 44.

A stylet 50 slides within the lumen 48 of hollow cannula 40. The distal tip 52 of stylet 50 may also be beveled at an angle corresponding to angle α of the distal tip 52 of cannula 40. It is preferred that distal tip 52 of stylet 50 be so beveled, but this is not necessary. If a beveled distal tip 52 is used for stylet 50, mechanisms within the handle which supports cannula 40 and stylet 50 are used to maintain the beveled distal tips 42 and 52 in proper rotational orientation with respect to one another. Thus, when stylet 50 is advanced distally within lumen 48 of cannula 40, distal tips 42 and 52 will be aligned to form a generally planar surface at the distal tip 32 of the instrument. The mechanisms for maintaining rotational orientation of stylet 50 and cannula 40 will be described subsequently in the application.

It will be appreciated from FIG. 4 that as stylet 50 advances distally toward distal tip 42 of cannula 40, superior haptic 24 will be expelled from slot 44.

Figure 2:
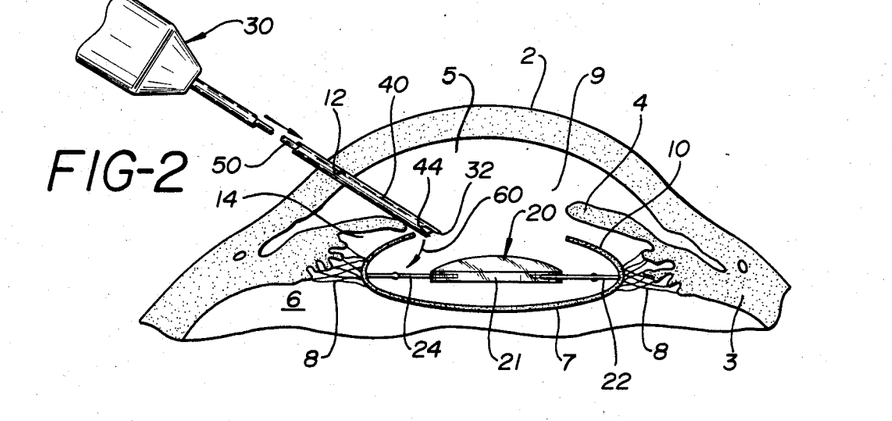
FIG. 2 shows the intraocular lens inserted in the eye.

As previously explained, both haptics are made of a resilient material. As lens 20 is inserted into the eye, haptics 22 and 24 tend to collapse toward optic 21 of lens 20. As haptics 22 and 24 are collapsed, energy is stored in them. As superior haptic 24 is expelled from slot 44, the forces exerted by resilient superior haptic 24 against the plane formed by the beveled distal tips 42 and 52 of cannula 40 and stylet 50 are resolved by the plane to cause superior haptic loop 24 to urge itself into the capsular bag in the direction shown by arrow 60 in FIG. 2.

Referring now to FIG. 5, there is shown a handle 70 in which cannula 40 and stylet 50 are supported. Handle 70 includes a cap 72, which is rigidly affixed to the distal end of handle 70 by means of cooperating threads 74 and 76.

A proximal portion 49 of lumen 40 is rigidly affixed to cannula hub 80. Cannula hub 80 has a bore 82 extending axially throughout its length into which proximal end 49 of cannula 40 may be fixed by a variety of means including braising, shown at 84, or press-fitting or other well-known means. Cannula hub 80 is generally cylindrical in shape and has a distal end 86 and a proximal end 87 and a keyway slot 88 in side wall 89 of hub 80.

Still referring to FIG. 5, there is shown a stylet hub 90 into which a proximal portion 54 of stylet 50 is fixed by means of braising 92 or press-fitting or other well-known means.

Stylet hub 90 has a generally cylindrical configuration with a distal portion 94, and intermediate portion 96 and a proximal portion 98. The diameter of proximal portion 98 is less than the diameter of intermediate portion 96. The diameter of distal portion 94 is also less than the diameter of intermediate portion 96. A keyway slot 97 also extends axially along the side wall 99 of stylet hub 90.

Handle 70 includes a bore 100 extending part way along its length. Bore 100 has three sections including a proximal portion 102 with a first diameter generally approximating the diameter of proximal stem portion 98 of stylus hub 90, an intermediate portion 104 with a diameter larger than that of proximal portion 102 and generally approximating the diameter of intermediate section 96 of hub 90 and a distal portion 106 having a diameter larger than that of intermediate portion 104 and generally approximating the diameter of cannula hub 80. The transition between proximal portion 102 and intermediate portion 104 of bore 100 forms a shoulder 108. A corresponding shoulder 93 at the transition between proximal stem portion 98 and intermediate portion 96 of hub 90 bottoms on shoulder 108. The transition between distal bore 106 and intermediate bore 104 forms a shoulder 110 against which the proximal surface 87 of cannula hub 80 bottoms.

Key pins 112 and 114 are mounted through handle 70 and project respectively into keyway 88 of cannula hub 80 and keyway 97 of stylet hub 90.

A spring 116 is placed between the confronting, proximal surface 87 of hub 80 and distal surface 118 of stylet hub 90.

The distal portion 94 of stylet hub 90 has a smaller diameter than the intermediate portion 96 of hub 90 to form a stem over which spring 116 fits.

Cap 72 holds cannula hub 80 in place against distal bore shoulder 110. Spring 116 biases stylet hub 90 against proximal bore shoulder 108.

Transverse slot 120 extends into handle 70 and communicates with the proximal portion 102 of bore 100. When stylet hub 90 is biased by spring 116 onto its most proximal position, stylet proximal stem 98 projects into handle transverse slot 120.

Still referring to FIG. 5, there is shown a lever 122 pivotably supported in transverse slot 120 by means of pin 124. A slot 126 extending through lever 122 receives a pin 128 which is fixed into handle 70 and extends across handle transverse slot 120. A cam surface 130 on the distal end of lever 122 engages the proximal surface of proximal stem 98 of stylet hub 90. Spring 116 biases stem 98 against cam surface 130, causing lever 122 to project out of handle transverse slot 120. Projection 140 extends from lever 122 toward the bottom of slot 120 and acts as a positive stop for lever 122 and correspondingly for arm 130 so that the position of the distal tip 52 of stylet 50 may be very precisely controlled. The positive stop feature provided by projection 140 makes it easier to precisely align the distal tip 52 and 42 of stylet 50 and cannula 40, respectively.

The top of lever 122 projects above the surface of handle 70 when projecting 140 bottoms in slot 120 so that the user can always feel lever 122. The top surface of lever 122 is preferably serrated or otherwise conditioned to provide good feel to the user.

Figure 7:
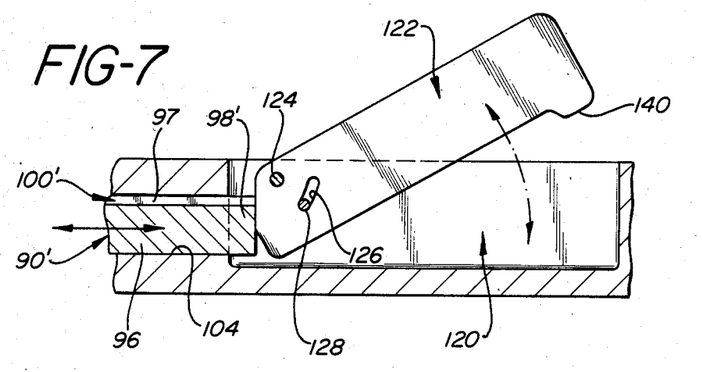
FIG. 7 shows a modification of the instrument of FIG. 5.

An alternative embodiment of a stylet hub 91 is shown in FIG. 7, which eliminates the proximal portion 98 of the embodiment shown in FIG. 5 and extends the intermediate portion 96 and correspondingly extends intermediate bore 104, thus eliminating proximal shoulder 108. Thus, the new proximal end portion 98 of the embodiment shown in FIG. 7 projects directly against the lever 122 and transmits the force of spring 116 directly to lever 122 to bias lever 122 directly in the up position. The embodiment shown in FIG. 7 is believed to improve tactile feel of the instrument which the surgeon may find more suitable. Keyway 100' extends completely along the intermediate portion of hub 90' to the proximal end of hub 90'.

In operation the inferior loop 22 and optic 21 are inserted into the eye by well known techniques. Superior loops 24 can either remain outside the eye or can be inserted into anterior chamber 5. Then the surgeon grasps the instrument 30 in his hand with his thumb or finger adjacent lever 122. With the lever 122 in the up position, the distal tip 52 of stylet 50 is positioned just proximally of the proximal end 46 of slot 44. The surgeon grasps haptic loop 24 in slot 44. If haptic 24 is still outside the eye, the surgeon inserts haptic loop 24 through incision 12 and maneuvers haptic loop 24 into a position past the superior edge of iris 4 and the superior edge of anterior flap 10 of capsular bag 7. If haptic 24 is already in anterior chamber 5, the tip of instrument 30 is inserted through incision 12, haptic 24 is grasped and inserted into capsular bag 7. Haptic 24 is captured in tapered slot 44 so that as haptic 24 is compressed inferiorly and optic 21 tends to rotate, haptic 24 will tend not to deflect laterally and thus, will tend not to slide out of slot 44. This tapered slot 44 provides better control over haptic 24 during insertion. Holding instrument 30 still, the surgeon merely depresses lever 122, causing it to rotate about pin 24 and causing cam surface 130 to urge stylet hub proximal stem 98 forward against the force of bias spring 116 and correspondingly causing distal tip 52 of stylet 50 to advance distally until it is aligned with distal tip 42 of cannula 40. Projection 140 bottoms on slot 120 to give a precise positive stop for distal tip 52 in proper alignment with distal tip 42.

In those cases where both the distal tips 52 and 42 of stylet 50 and cannula 40 are beveled at a corresponding angle, a planar surface will be formed by the aligned surfaces of cannula distal tip 42 and stylet distal tip 52. When superior haptic 24 is ejected from slot 44, a force is exerted by resilient superior haptic 24 against the plane formed by the combined distal tips 42 and 52 of cannula 40 and stylet 50, respectively. This distal plane acts to resolve the force to cause superior haptic 24 to urge itself into capsular bag 7 in the direction indicated by arrow 60 in FIG. 2.

Figure 6:
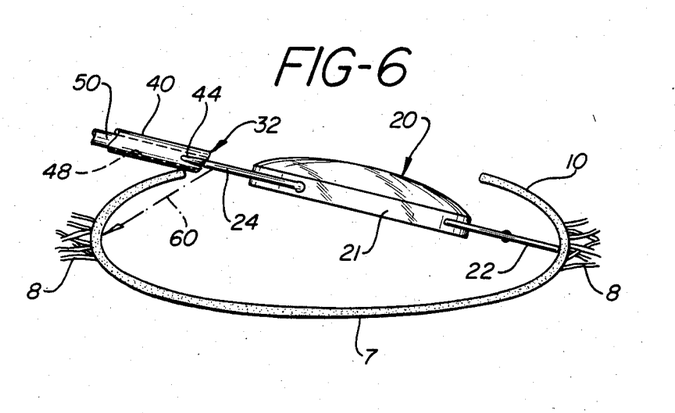
FIG. 6 shows an enlarged view of a portion of the eye and the tool shown in FIG. 1.

Referring to FIG. 6, there is shown an enlarged schematic view of the instrument of the present invention introducing superior 24 into capsular bag 7. It can be seen that as stylet 50 advances toward the tip 42 of annula 40, superior haptic 24 will urge itself in the direction of arrow 60, shown in FIG. 6, into the capsular bag.

Handle 70, cannula 40, stylet 50, cap 72, hubs 80 and 90 and the other components of this instrument are preferably made of surgical metal, preferably stainless steel, or some other material which is capable of being sterilized in an autoclave. However, it is possible that certain portions of instrument 30, particularly stylet 50, can be made of more flexible materials like plastic.

It is also possible that at least a portion of cannula 40 can be curved to facilitate insertion into the eye and handling of superior haptic 24. In those instances where cannula 40 is curved, it is desirable to have stylet 50 made of a flexible material like plastic or very flexible metal so that it will readily conform to the curved shape of cannula 40 as stylet 50 is advanced distally along cannula 40.

Figure 8:
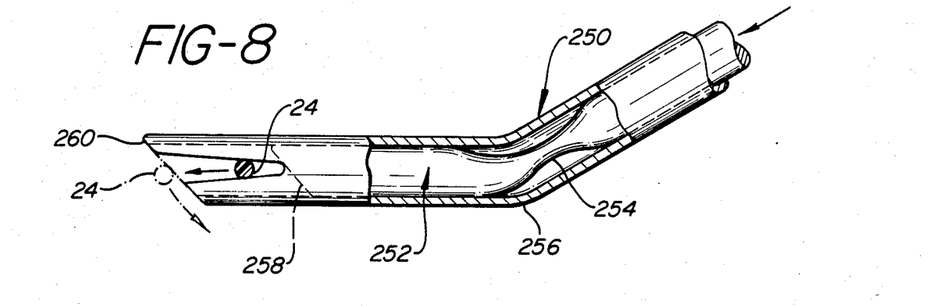
FIG. 8 shows a modified insertion tool.

Referring now to FIG. 8, there is shown an alternative embodiment of the present invention with a bent cannula 250, preferably bent at an angle of about 30°, although this angle is not critical and any convenient angle could be used. A stylet 252 can be made of a flexible material like plastic. Alternatively, a rigid material could be used which has a reduced cross-section in area 254 in the vicinity of the bend 256 of cannula 250. This area of reduced cross-section would be sufficiently trimmed to allow a distal movement of the stylet 252 sufficient to allow the distal tip 258 of stylet 252 to be aligned wtih the distal tip 260 of bent stylet 250.

Figure 9:
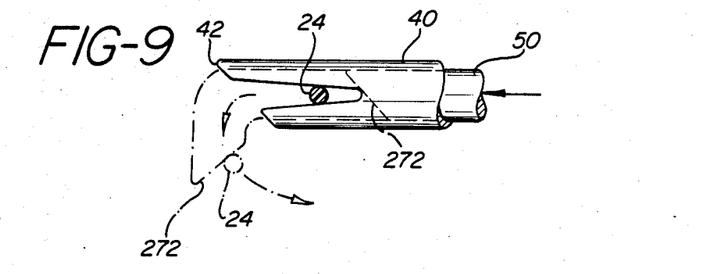
FIG. 9 shows a further modified insertion tool.

Referring now to FIG. 9, a further alternative embodiment of the stylet 50 is shown in which the distal region 270 of stylet 50 is prestressed so that when it clears the beveled distal tip 42, of cannula 40, the beveled distal tip 272 of stylet 50 will rotate in the direction which one wishes to urge the superior haptic 24. When stylet 50 is retracted, the prestressed tip portion 272 will merely be withdrawn into cannula 40.

In a further alternative embodiment, stylet 50 could be a fiber optic bundle suitably connected to a light source and camera (not shown) to illustrate and photograph the interior of the eye during lens insertion.

In a further alternative embodiment, the manually actuated lever 122 could be replaced by a mechanism by using, for example, a pneumatic actuator operated by a foot switch to advance the stylet 50.

Figure 10A:
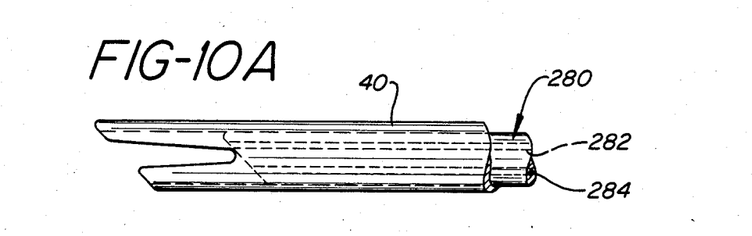
FIGS. 10A and 10B shows a further modified insertion tool.
Figure 10B:
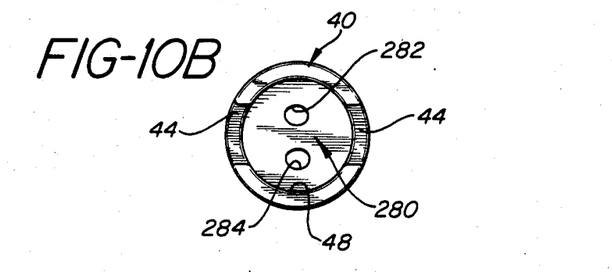

In a further alternative embodiment, shown in FIG. 10, stylet 280 could incorporate irrigation and or aspiration channels 282 and 284, respectively, through which fluid could be introduced to or taken from the eye during surgery. The irrigation fluid could provide lubrication and additional thrust to urge the superior loop 24 off the tip of the instrument. These irrigation and aspiration channels would be connected to irrigation/aspiration apparatus which are well known in the industry and are, therefore, not shown in the present application.

It can be seen that the instrument of the present invention provides a reliable device for inserting the superior haptic loop of an intraocular lens into the capsular bag of the eye while minimizing wrist or finger rotation that the surgeon must use to release the haptic loop and, theefore, tending to protect the interior anatomy of the eye.

The present invention has been described in conjunction with preferred embodiments. Those skilled in the art will appreciate that many modifications and changes may be made to the preferred embodiments without departing from the present invention. It is, therefore, not intended to limit the present invention except as set forth in the appended claims.

I claim:

1. A surgical instrument tip to facilitate the insertion of the resilient haptic loop of an intraocular lens into the eye comprising;
    a hollow cannula having a generally circular cross section, and having a proximal end, a distal end and a lumen extending throughout its length;
    said distal end of said cannula beveled at an angle to the adjacent wall of said cannula so that the distal end of the beveled cannula defines an ellipse;
    said distal end of said cannula also including a slot extending generally proximally from the distal tip for holding one of said haptic loops of said intraocular lens while said loop is maneuvered into the desired position in the eye, said slot aligned generally along the minor axis of said ellipse defined by the beveled end of said cannula;
    a stylet slidably disposed within the lumen of said cannula and having a proximal end and a distal end;
    means for positioning the distal end of said stylet slightly proximally of the proximal end of said slot; and
    means for advancing said stylet distally until said distal end of said stylet is aligned to eject said haptic loop from said cannula slot;
    whereby the force exerted by the resilient haptic loop against the distal tip of said instrument will cause said haptic loop to urge itself into the desired position in the eye.

2. The instrument of claim 1 wherein the distal end of said stylet is beveled at an angle to the adjacent wall of said stylet generally corresponding to the bevel angle of said distal end of said cannula and further including:
    means for circumferentially orienting said stylet and said cannula so that the beveled distal ends of said stylet and said cannula are aligned to form a plane at the distal tip of said instrument;
    whereby the force exerted by said resilient haptic loop against said plane will be resolved by said plane to cause said haptic loop to urge itself into the capsular bag of the eye.

3. The instrument of claim 2 further including a handle having a bore extending at least partially along its length said handle receiving and supporting proximal portions of said cannula and said stylet.

4. The instrument of the claim 3 wherein the means for advancing said stylet includes means operatively supported on said handle for engaging a proximal portion of said stylet for urging said stylet distally a predetermined distance so that the beveled distal end of said stylet will align itself with the beveled distal end of said cannula to eject said haptic loop from said cannula slot.

5. The instrument of claim 3 wherein the said means for circumferentially orienting said stylet and said cannula include cooperative means on said handle and a proximal portion of said cannula including a hub rigidly attached to a proximal portion of said cannula and adapted to be received into said handle bore, said hub having a distal portion, a proximal portion and a surrounding sidewall;
    a keyway slot in said cannula hub sidewall;
    a key pin extending into said handle bore and engaging said cannula hub keyway slot to control rotational movement of said cannula with respect to said handle; and,
    further including cooperating means on said handle and a proximal portion of said stylet including a hub rigidly attached to a proximal portion of said stylet and adapted to be received into said handle bore, said stylet hub having a distal portion, a proximal portion and surrounding sidewall;
    a keyway slot in said stylet hub sidewall;
    a key pin extending into said handle bore and engaging said stylet hub keyway slot to control rotational movement of said stylet with respect to said handle.

6. A surgical instrument tip to facilitate the insertion of the resilient haptic loop of an intraocular lens into the eye comprising:
   a hollow cannula having a proximal end, a distal end and a lumen extending throughout its length;
   said distal end of said cannula beveled at an angle to the adjacent wall of said cannula;
   said distal end of said cannula also including a slot extending generally proximally from the distal tip for holding one of said haptic loops of said intraocular lens while said loop is maneuvered into the desired position in the eye;
   a stylet slidably disposed within the lumen of said cannula and having a proximal end and a distal end wherein the distal end of said stylet is beveled at an angle to the adjacent wall of said stylet generally corresponding to the beveled angle of the distal end of said cannula;
   means for positioning the distal end of said stylet slightly proximally of the proximal end of said slot;
   means for circumferentially orienting said stylet and said cannula so that the beveled distal ends of said stylet and said cannula are aligned to form a plane at the distal tip of said instrument;
   means for advancing said stylet distally until said distal end of said stylet is aligned to eject said haptic loop from said cannula slot;
   whereby the force exerted by said resilient haptic loop against said plane will be resolved by said plane to cause said haptic loop to urge itself into the capsular bag of the eye.

7. The instrument of claim 6 wherein at least a portion of said cannula curves at a desired radius and said stylet is made of a flexible material so that it will readily conform to the curvature of said cannula as it is urged forward by said advancing means.

8. The instrument of claim 6 wherein at least a portion of said cannula curves at a desired radius and said stylet is rigid and includes a corresponding curve and wherein the cross-section of said stylet in the vicinity of said curve is reduced in order to permit the distal end of said stylet to be advanced distally a sufficient distance to permit said haptic loop to be ejected from said cannula slot before said stylet binds at the curved portion of said cannula.

9. The instrument of claim 6 further including means for retracting said stylet from its advanced position to a position proximal of said slot.

10. The instrument of claim 6 wherein said slot in the distal end of said cannula tapers from the distal end of said cannula proximally so that said slot becomes narrower as it extends proximally from said cannula distal end.

11. The instrument of claim 6 wherein said advancing means includes a pneumatic actuator.

12. The instrument of claim 6 further including a handle having a bore extending thereinto, said bore having:
   an intermediate portion with a first diameter; and,
   a distal portion with a larger diameter;
   the transition between said distal bore and said intermediate bore forming a distal flange,
   said handle further including a slot extending transversely into the side of said handle and communicating with the intermediate portion of said handle bore;
   a stylet hub rigidly attached to a proximal portion of said stylet and having an intermediate portion with a diameter corresponding generally to the intermediate portion of said handle bore;
   a proximal portion of said stylet rigidly affixed to a distal portion of said stylet hub;
   said stylet hub intermediate portion extending through said intermediate portion of said handle bore into said transverse handle slot;
   a cannula hub rigidly attached to a proximal portion of said cannula and slidably received in the distal portion of said handle bore and bottoming on said distal flange;
   means disposed in said handle transverse slot and operatively engaging the proximal surface of said stylet hub proximal stem for advancing said stylet hub and, correspondingly, the distal tip of said stylet to eject said resilient haptic loop from said slot in the distal tip of said cannula.

13. The instrument of claim 12 wherein the diameter of said handle bore proximal portion is less than the diameter of said handle bore intermediate portion and wherein the stylet hub proximal portion diameter is less than the diameter of said stylet hub intermediate portion to form a proximal stem on said stylet hub, said stem freely slidable within said hub bore proximal portion; and
   wherein the transition between said intermediate and said proximal portions of said handle bore form a generally radially extending flange which acts as a stop for the proximally facing portion of the intermediate portion of said style hub.

14. The instrument of claim 13 wherein said stylet hub stem extending into said transverse slot;
   a lever pivotably disposed in said handle transverse slot and including a cam surface abutting the proximally-facing surface of said stylet hub stem;
   said lever adapted to advance said stylet distally a predetermined distance to align said distal tip of said style with said distal tip of said cannula.

15. The instrument of claim 12 further including a lever pivotably disposed in said handle transverse slot and including a cam surface abutting the proximally-facing surface of said style hub;
   said lever adapted to advance said style distally a predetermined distance to align said distal tip of said stylet with said distal tip of said cannula.

16. The instrument of claim 15 further including a pin extending across said handle transverse slot; and,
   a slot in said lever through which said transverse pin projects to provide a stop for controlling the position of said lever.

17. The instrument of claim 15 further including a projection on said lever extending toward the bottom of said transverse slot and adapted to bottom thereon to provide a positive stop for said lever to control the distal movement of said stylet.

18. The instrument of claim 6 wherein said stylet is made of a flexible material and the distal portion of said stylet is prestressed to assume a rest position wherein the distal portion of said stylet extends in a direction generally transverse to the axis of said stylet;
   said stylet distal portion being axially aligned with the adjacent portion of said style when said stylet is disposed within said cannular lumen;
   whereby when said stylet is advanced distally to as to clear the distal end of said cannula said prestressed distal portion of said stylet will tend to assume its rest position and to curve transversely out of said cannula to eject said haptic loop from said cannula slot in a preferred direction.

19. The instrument of claim 6 wherein said stylet includes a fiber optic bundle suitable for connection to a light source to illuminate the interior of the eye during lens insertion.

20. The instrument of claim 6 wherein said stylet includes an irrigation channel extending along its length to introduce fluid into the eye through said instrument.

21. The instrument of claim 20 wherein said stylet further includes an aspiration channel extending therealong to aspirate fluid from the eye.

* * * * *